(12) United States Patent
Shim et al.

(10) Patent No.: US 8,513,011 B2
(45) Date of Patent: Aug. 20, 2013

(54) METHODS AND COMPOSITIONS FOR CULTURING CARDIOMYOCYTE-LIKE CELLS

(75) Inventors: Winston Se Ngie Shim, Singapore (SG); Philip En Hou Wong, Singapore (SG)

(73) Assignee: Biotech Research Ventures Pte Limited, Singapore (SG)

( * ) Notice: Subject to any disclaimer, the term of this patent is extended or adjusted under 35 U.S.C. 154(b) by 1310 days.

(21) Appl. No.: 11/210,950

(22) Filed: Aug. 24, 2005

(65) Prior Publication Data

US 2006/0057124 A1 Mar. 16, 2006

Related U.S. Application Data

(60) Provisional application No. 60/604,651, filed on Aug. 26, 2004.

(51) Int. Cl.
*C12N 5/00* (2006.01)
(52) U.S. Cl.
USPC ........... 435/377; 424/93.7; 435/325; 435/375
(58) Field of Classification Search
None
See application file for complete search history.

(56) References Cited

U.S. PATENT DOCUMENTS

| | | | | |
|---|---|---|---|---|
| 5,736,396 A | * | 4/1998 | Bruder et al. | 435/366 |
| 5,741,701 A | * | 4/1998 | Swiderek et al. | 435/297.1 |
| 5,770,690 A | * | 6/1998 | Bitler et al. | 530/324 |
| 5,855,619 A | * | 1/1999 | Caplan et al. | 623/23.72 |
| 6,057,426 A | * | 5/2000 | Lesslauer et al. | 530/351 |
| 6,083,920 A | * | 7/2000 | Rosenberg | 514/25 |
| 6,150,163 A | * | 11/2000 | McPherson et al. | 435/384 |
| 6,387,369 B1 | * | 5/2002 | Pittenger et al. | 424/93.7 |
| 2002/0137900 A1 | * | 9/2002 | Ferrara et al. | 530/399 |
| 2003/0031651 A1 | * | 2/2003 | Lee et al. | 424/93.7 |

OTHER PUBLICATIONS

Pittenger MF et al. 1999. Multilineage potential of adult human mesenchymal stem cells. Science 284: 143-147.*
Rangappa S et al. 2003. Cardiomyocyte-mediated contact programs human mesenchymal stem cells to express cardiogenic phenotype. J Thorac Cardiovasc Surg 126: 125-132.*
Xu W. et al. 2004. Mesenchymal stem cells from adult human bone marrow differentiate into a cardiomyocyte phenotype in vitro. Exp Biol Med 229: 623-631.*
Grigoriadis AE et al. 1988. Differentiation of muscle, fat, cartilage, and bone from progenitor cells present in a bone-derived clonal cell population: effect of dexamethasone. J Cell Biol 106: 2139-2151.*
Welder AA et al. 1995. Toxic effects of anabolic-androgenic steroids in primary rat hepatic cell cultures. J Pharmacol Toxicol Methods 33: 187-195.*
Beltrami et al., "Adult Cardiac Stem Cells are Multipotent and Support Myocardial Regeneration," *Cell* 114:763-776 (2003).
Beltrami et al., "Evidence That Human Cardiac Myocytes Divide After Myocardial Infarction," *N. Engl. J. Med.* 344:1750-1757 (2001).
Bossolasco et al., "Skeletal Muscle Differentiation Potential of Human Adult Bone Marrow Cells," *Exp. Cell. Res.* 295:66-78 (2004).
Liu et al., "Growth and Differentiation of Rat Bone Marrow Stromal Cells: Does 5-Azacytidine Trigger Their Cardiomyogenic Differentiation?" *Cardiovasc. Res.* 58:460-468 (2003).
Urbanek et al., "Intense Myocyte Formation from Cardiac Stem Cells in Human Cardiac Hypertrophy," *Proc. Natl. Acad. Sci. USA* 100:10440-10445 (2003).

* cited by examiner

*Primary Examiner* — Lora E Barnhart Driscoll
(74) *Attorney, Agent, or Firm* — Kathleen D. Rigaut; Dann, Dorfman, Herrell and Skillman, P.C.

(57) ABSTRACT

The present invention provides cardiomyocyte-like cells that have been cultured from populations of bone marrow cells. The culture method includes the use of defined media that are free of agents such a 5-azacytidine. The cardiomyocyte-like cells can be engrafted to heart tissue to repair damage resulting from an ischaemic episode.

12 Claims, 13 Drawing Sheets

METHODS AND COMPOSITIONS FOR CULTURING CARDIOMYOCYTE-LIKE CELLS

This application claims benefit of U.S. Provisional Patent Application Ser. No. 60/604,651, filed Aug. 26, 2004, which is hereby incorporated by reference in its entirety.

FIELD OF THE INVENTION

The present invention relates to methods for culturing mammalian cells for use in therapeutic applications. More specifically the present invention is concerned with methods and compositions for producing cell populations useful in the treatment of damaged myocardial tissue.

BACKGROUND TO THE INVENTION

The heart is a vital organ, being responsible for pumping oxygenated and nutrient rich blood to the body. Efficient functioning of the heart can be compromised by trauma, infection and ischaemia. Ischaemic heart disease is the leading cause of death in industrialised countries, often manifesting clinically as a myocardial infarction (MI). The management of ischaemic heart disease essentially relies upon one of three strategies, including medical therapy, percutaneous coronary intervention (PCI) and coronary artery bypass grafting. Although medical treatment remains the mainstay of anti-ischaemic therapy, many patients undergo additional, invasive therapy in an attempt to restore coronary blood flow.

While there has been some success in preventing second and subsequent myocardial infarctions, acute MI strikes the majority of sufferers without prior warning. It is generally not possible to predict (and therefore prevent) a primary infarction, with the inevitable result being that a certain amount of irreparable damage to cardiac tissue occurs.

Mammalian heart has been considered terminally differentiated with a static number of cardiomyocytes that are incapable of self-renewal. There is emerging evidence that limited number of replicating cardiomyocytes and stem cells are participating in the process of cellular maintenance and myocardial regeneration in patients with heart failure. Beltrami, A. P., Urbanek, K., Kajstura, J., Yan, S. M., Finato, N., Bussani, R. et al. Evidence that human cardiac myocytes divide after myocardial infarction. *N Engl J Med.* 2001; 344:1750-7. Urbanek, K., Quaini, F., Tasca, G., Torella, D., Castaldo, C., Nadal-Ginard, B. et al. Intense myocyte formation from cardiac stem cells in human cardiac hypertrophy. *Proc Natl Acad Sci USA.* 2003; 100:10440-5. However, the numbers of cells involved in this process are believed to have insignificant effect in the repair of major injuries such as myocardial infarction. There is therefore a clear need in the art for methods to repair damaged myocardium after an ischaemic event or that due to other causes of myocardial damage.

It is an aspect of the present invention to at least alleviate a problem of the prior art by providing specific cells directed towards a lineage suitable for repair of the myocardium.

SUMMARY OF THE INVENTION

In one aspect of the present invention provides a method for culturing a cardiomyocyte-like cell the method comprising providing a human bone marrow cell population or cell population derived therefrom, and culturing the cell population under conditions leading to an increase in the number of cardiomyocyte-like cells in the culture. Without wishing to be limited by theory it appears that appropriate culture of a mesenchymal stem cell found in bone marrow leads to the production of cardiomyocyte-like cells that may be used to repair the heart after an ischemic event.

In another aspect the present invention provides a medium suitable for culturing bone marrow to produce cardiomyocyte-like cells. Applicants have found that cardiomyocyte-like cells may be cultured without the use of differentiating agents such as 5-azacytidine, or conditioned medium. The medium may comprise supplements selected from the group consisting of dexamethasone, insulin, an iron source, a trace element, a fatty acid, and an antioxidant either alone or in any combination.

A further aspect of the invention provides a cardiomyocyte-like cell cultured from bone marrow, the cell expressing a protein selected from the group consisting of sarcomeric α-actin, sarcomeric α-actinin, desmin, skeletal/cardiac specific titin, sarcomeric α-tropomyosin, cardiac troponin I, sarcomeric MHC, SERCA2 ATPase and connexin-43 either alone or in any combination.

Also included in the scope of the present invention are methods for treating a heart condition relating to damage of a cardiomyocyte, the method comprising administering to a subject in need thereof an effective number of cardiomyocyte-like cells as described herein. Of particular advantage, the cardiomyocyte-like cells may be removed from a hollow bone of the subject, cultured to increase the number of cardiomyocyte-like cells, and then administered by direct injection to the myocardium. This entire method can be performed percutaneously resulting in reduced trauma to the subject, and obviates the problem of immunological rejection of the engrafted cells.

Figure 1:
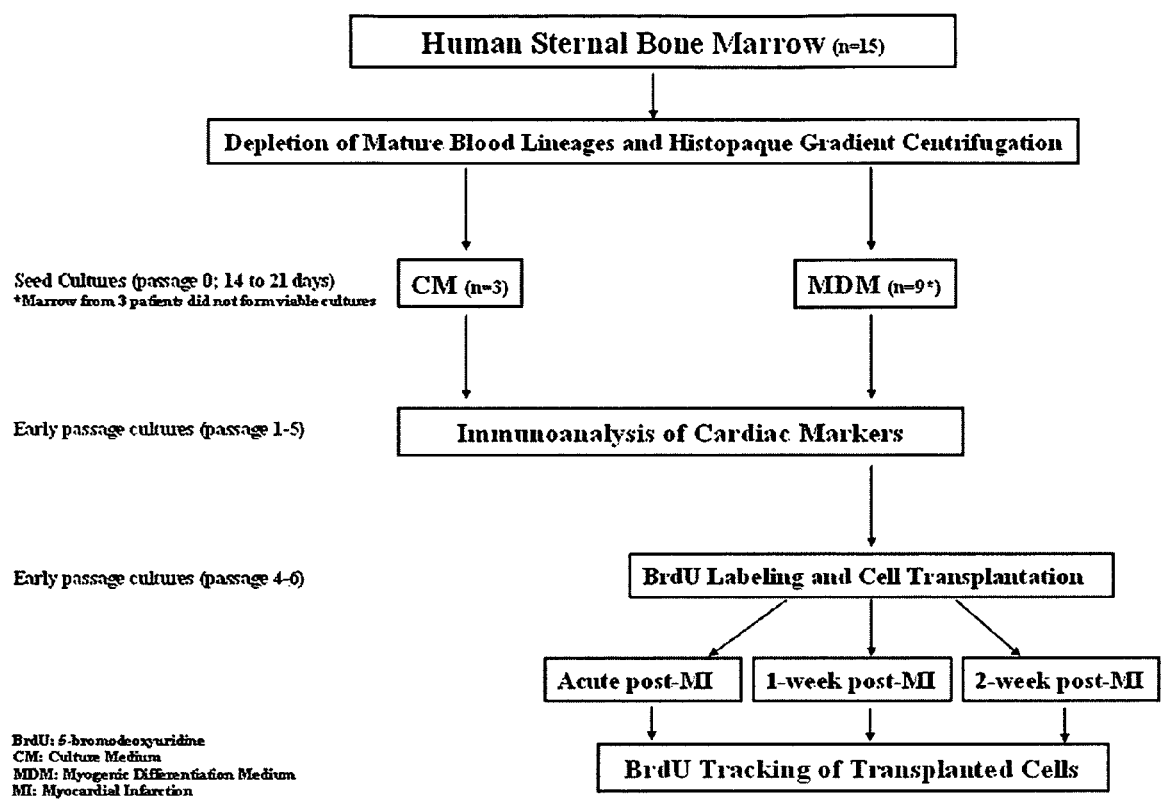
FIG. 1 is a flow chart detailing the isolation and characterization of human sternal bone marrow-derived cardiomyocyte-like cells.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

DETAILED DESCRIPTION OF THE INVENTION

In a first aspect, the present invention provides a method for culturing a cardiomyocyte-like cell (CLC) the method comprising providing a human bone marrow cell population or cell population derived therefrom, and culturing the human bone marrow cell population or cell population therefrom under conditions leading to an increase in the number of cardiomyocyte-like cells (CLCs) in the culture.

Applicants have found that cells of the bone marrow may be used to prepare populations of cardiomyocyte-like cells in an in vitro system. It appears that adult bone marrow may contain multipotent stem cells that are capable of participating in regenerative tissue repair. A specific population of cardiomyocyte-like cells with intrinsic myocardial characteristics can therefore be derived from human adult bone marrow. These specific cells have been demonstrated to engraft into cardiac myofibers in the infarcted myocardium.

As used herein, the term "cell population" is intended to include a population of one cell or a population of many cells. The cell population may be homogenous or heterogenous with respect to cell phenotype. Included in the method is the use of cells derived from a human bone marrow cell population, including progeny cells resulting from the replication of a cell in the human bone marrow cell population. It is also possible that the derived cells have not replicated but have attained an altered phenotype, possibly due to maturation or differentiation. The progeny cell population may have the same or similar homogeneity or heterogeneity as the human bone marrow cell population.

Without wishing to be limited by theory it is thought that the source of nascent CLCs is a multipotent mesenchymal stem cell (MSC). The bone marrow stem cells isolated conform to the published characteristics of mesenchymal stem cells, that is they started as sparsely isolated single cells and go on to form confluent colony of spindle cells. These putative mesenchymal stem cells stained positive to a panel of markers that are widely accepted as cellular markers of mesenchymal stem cells. For example, the cells are positive for CD44, CD90, CD105, CD106 and negative for CD45, CD117, FLT1, and TIE2.

These cultured mesenchymal stem cells also display multi-lineage differentiation potential. They have the ability to differentiate into bone cells when induced in define osteogenic medium and they are able to differentiate into fat cells when cultured in adipogenic induction medium.

These mesenchymal stem cells also differentiate into CLCs with a number of cardiac markers when cultured in appropriate induction medium. While similarly isolated early passage mesenchymal stem cells cultured in normal medium did not show sign of cardiac differentiation (Table 2 in the text).

Figure 6:
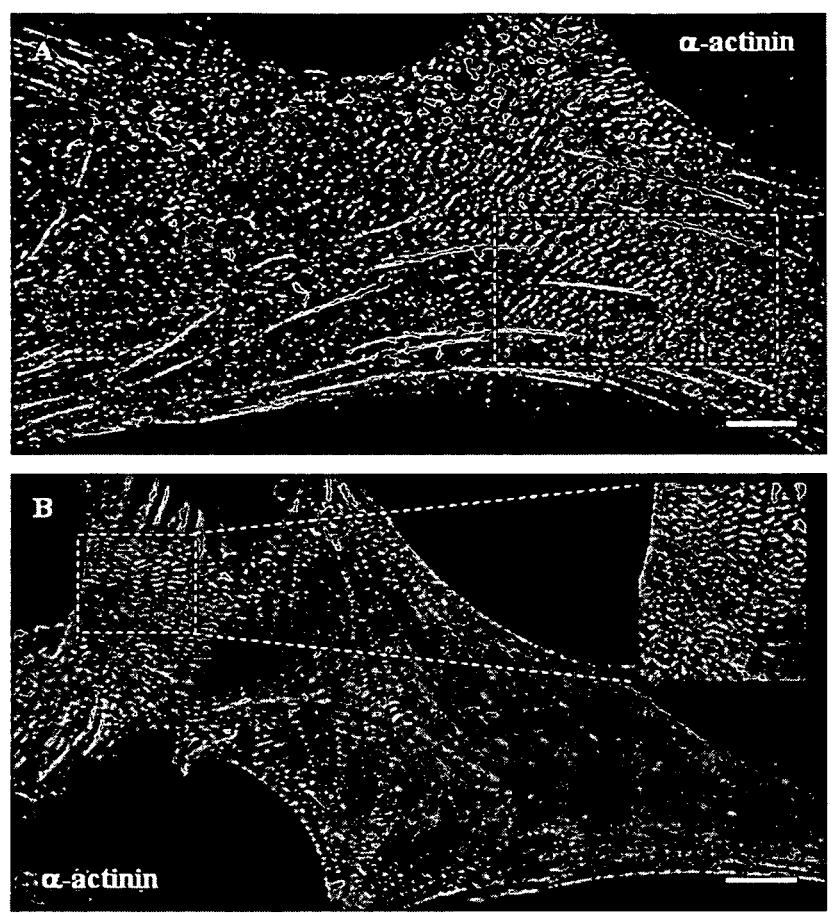
FIGS. 6(A) and (B) are immunofluorescence micrographs of human cardiomyocyte-like cells showing characteristic cardiomyocyte phenotype with sarcomeres and nascent Z-bands. (A) lateral alignment of sarcomeric α-actinin-positive aggregates of Z-bodies into cross-striations (box) in a cardiomyocyte-like cell. (B) formation of sarcomeres with regular periodicities between Z-bands of a cardiomyocyte-like cell. Insert: magnification of the selected area in B showing highly organized Z-bands. Scar bar, 10 μm.

Furthermore, these mesenchymal stem cells (following differentiation into CLCs) gradually organise their cytoskeleton into early sarcomeres by staining positive to alpha actinin in a striated pattern (FIG. 6).

Accordingly, in a preferred form of the method the human bone marrow cell population or cell population derived therefrom comprises a MSC. In one form of the invention the MSC expresses one or more of the following markers: CD44, CD90, CD105 and CD106. Furthermore, the MSC may exhibit adherent-dependent growth or a spindle morphology. After subsequent passaging the MSC may attain a polygonal morphology.

Without wishing to be limited by theory it is also possible that the source of nascent CLCs may be a rare myocardial progenitor cell that is pre-existing in the bone marrow. Therefore, in an alternative form of the method, the human bone marrow cell population or cell population derived therefrom comprises a myocardial progenitor cell.

It should also be considered that the source of nascent CLCs is a combination of MSCs and rare myocardial progenitor cells.

The source of bone marrow for use in the present method may be obtained from a bone in any part of the body such as the iliac crest but in a preferred form of the method the marrow is from the sternum. The use of bone marrow from the sternum has the advantage that it may be obtained during heart surgery while the thoracic cavity is opened.

The skilled person will understand that it is not strictly necessary to use a cell population taken directly from bone marrow cells present in the hollow of a bone. The bone marrow is not completely isolated from the circulatory system, and it is possible to obtain bone marrow cells from other sources, such as the peripheral blood (peripheral blood stem cells; PBSC). The PBSC may be collected and used in certain situations as a source of stem cells for transplantation.

Another source of stem cells may be the blood found in the placenta of a newborn baby once the umbilical cord is cut. Umbilical cord blood (UCB) has been successfully used as a source of bone marrow stem cells for transplantation in both related and unrelated patients.

It should be understood that the bone marrow cell population may be treated in any suitable manner before culturing. For example, the cell population could be concentrated or diluted to a desired concentration, washed to remove unwanted solvents, solutes, protein contaminants or treated to remove unwanted cell types. In one form of the method the bone marrow cell population is treated to remove mature cells of a blood lineage. The skilled person will be familiar with a range of preparative methods potentially useful in this regard including fluorescence activated cell sorting (FACS), antibody "panning", chromatographic methods, physical methods such as centrifugation incorporating materials such as Histopaque and Percoll. Immunological-based methods such as FACS and panning are possibly the most discriminating since cells can be sorted by the presence or absence of specific cell surface markers.

The culture of the cell population can take place in any suitable cell culture vessel. A wide range of cell culture vessel substrates and configurations are known to the skilled person, and it is well within the ordinary skill in the art to select an appropriate vessel. For larger scale culture of cells, vessels such as roller bottles, or multilayered "cell factories" may be used. For smaller scale culture, simple T-flasks will be appropriate. Preferably, the substrate is such that it allows adherence and growth of CLCs, however the method also contemplates the use of adherence factors such as collagen where appropriate.

An advantage of the present invention is that CLCs can be produced with relatively simple defined cell culture medium, and without the use of toxic differentiating agents such as 5-azacytidine. Furthermore, there is no need to co-culture the cells with other cells of a cardiac lineage (such as rat myocytes) to stimulate differentiation. Co-culturing technique and 5-aza treatment are not likely to be applicable clinically due to their low efficacy and potentially harmful effects arising from nonspecific demethylation effect of 5-azacytidine. Liu, Y., Song, J., Liu, W., Wan, Y., Chen, X. & Hu, C. Growth and differentiation of rat bone marrow stromal cells: does 5-azacytidine trigger their cardiomyogenic differentiation? *Cardiovasc Res.* 2003; 58:460-8. Our study shows that human adult bone marrow cells can be successfully differentiated towards CLCs with defined myocardial characteristics using a simple culture medium independent of 5-aza treatment or co-culturing technique. Furthermore, the intrinsic cardiomyocyte-like characteristics may enhance the ability of CLCs to directly engraft as cardiomyocytes in transplanted myocardium.

One particularly useful base culture medium is Dulbecco's Modified Eagle's Medium-Low Glucose (DMEM-LG), augmented with foetal bovine serum. Another useful base medium is MCDB201. In a highly preferred form of the invention the base culture medium comprises about 60% DMEM-LG and 28% MCDB-201. For cells to attain optimal phenotypic qualities it is desirable to add serum to the base culture medium. The addition of serum provides hormones, transport proteins, trace elements and the like, and it is possible to ascertain the optimum concentration of serum in the medium purely by routine experimentation. In one form of the method the serum is present at a concentration of about 10%.

Applicants have found that certain supplements may be added to the base medium to improve the quality of the cells. Suitable supplements include insulin, an iron source, a trace element, a fatty acid, dexamethasone, and an antioxidant. In a highly preferred form of the method the iron source is transferrin, the fatty acid is linoleic acid, the trace element is selenium and the antioxidant is ascorbate. Of course, the skilled artisan could determine that the addition of other supplements or the substitution with similar supplements may give advantageous results. Such routine modifications to the culture medium are included within the scope of this application. For example, ethanolamine or oleic acid may be used as the fatty acid in place of linoleic acid. Similarly, sodium pyruvate could be added as an additional energy source, or further buffers may be added to maintain pH at an optimum level.

The culture can continue for any period of time so long as the medium is changed whenever necessary to ensure the viability of the cells. In one form of the method, the cells are cultured for about 7 days to about 10 days at 37° C. in 5% $CO_2$ before further use. More preferably, the cultures are maintained until confluence is reached in about 14 to 21 days after the initial seeding.

In another aspect, the present invention provides a cardiomyocyte-like cell produced according to the methods described herein. As used herein, the term "cardiomyocyte-like cell" is intended to include any cell that is able to fulfill a function in myocardial tissue. The cell may be able to fulfill the function directly after culturing, or after some further treatment (e.g. exposure to a differentiation agent, passaging, engrafting to the heart). The cardiomyocyte-like cell may express one or more of the following cardiomyocyte-specific proteins at levels sufficient to be detected immunologically: sarcomeric α-actin, sarcomeric α-actinin, desmin, skeletal/cardiac specific titin, sarcomeric α-tropomyosin, cardiac troponin I, sarcomeric MHC, SERCA2 ATPase and connexin-43. The CLCs of the present invention show extensive expression of cardiac proteins and therefore clearly differ from previously reported undifferentiated human MSCs that showed no myocardial gene expression. Rangappa, S., Entwistle, J. W., Wechsler, A. S. & Kresh, J. Y. Cardiomyocyte-mediated contact programs human mesenchymal stem cells to express cardiogenic phenotype. *J Thorac Cardiovasc*

Surg. 2003; 126:124-32. Furthermore, expression of α-MHC, a specific marker for adult cardiomyocytes, together with lack of skeletal MHC and MyoD expression indicate that CLCs are different from skeletal muscle stem cells that were previously reported to reside in bone marrow. Bossolasco, P., Corti, S., Strazzer, S., Borsotti, C., Del Bo, R., Fortunato, F. et al. Skeletal muscle differentiation potential of human adult bone marrow cells. *Exp Cell Res.* 2004; 295:66-78. In addition, the formation of cross-striated Z-bands also indicates a nascent cardiomyocyte phenotype. However, the absence of spontaneous beating in culture suggests the CLCs have not fully differentiated into mature cardiomyocytes. Similar observations have been reported in cultured Lin$^-$/c-Kit$^+$ cardiac-derived stem cells, Beltrami, A. P., Barlucchi, L., Torella, D., Baker, M., Limana, F., Chimenti, S. et al. Adult cardiac stem cells are multipotent and support myocardial regeneration. *Cell.* 2003; 114:763-76, suggesting that mature cardiomyocyte phenotype may require further differentiation in a proper cardiac milieu.

In one form of the invention the CLCs express one or more of the following markers: CD44, CD90, CD105 and CD106. Furthermore, the CLCs may exhibit adherent-dependent growth or a spindle morphology. Importantly, the cardiomyocyte-like cells produced by the present methods are capable of forming a viable engraftment of cardiac myofibers when administered to the heart.

Of course, the cell populations or the resultant cardiomyocyte-like cells described herein may be frozen in liquid nitrogen for the purposes of preservation. The skilled artisan is sufficiently familiar with the use of cryoprotectants such as DMSO, and programmable biological freezers to allow freezing of any cell described herein.

In another aspect the present invention provides a defined culture medium when used for culturing a cardiomyocyte-like cell according to the method of claim 1 substantially free of 5-azacytidine. Preferably, the medium is free of a biological agent secreted from a rat myocyte.

The medium can be based on any of the basal media known to the skilled person, however a preferred medium is based on Dulbecco's Modified Eagle's Medium-low glucose (DMEM-LG) or MCDB-201 augmented with foetal bovine serum. In a highly preferred form of the invention the base culture medium comprises about 60% DMEM-LG and 28% MCDB-201.

The medium may comprise a supplement such as dexamethasone, insulin, an iron source, a trace element, a fatty acid, and an antioxidant either alone or in any combination. Highly preferred supplements include transferrin, linoleic acid, and ascorbate either alone or in any combination.

In a further aspect the present invention provides a method for preparing a cell population for use in repairing damaged cardiac tissue in a subject, the method including obtaining a bone marrow cell population from an autologous subject or a donor. The skilled person will appreciate that heterologous cells may also be used subject to histocompatibility issues.

In another aspect the present invention provides a method for treating damage to myocardial tissue, the method comprising administering to a subject in need thereof an effective number of cells committed to a cardiomyocyte lineage. Applicants have found that engraftment may be more successful if cells that have at least partially differentiated toward a cardiac myocyte lineage are used. In a preferred form of the method the cells are as described herein, and more preferably are produced according to a method described herein.

The damage to myocardial tissue may be the result or potential result of any physical, biological, immunological or chemical agent including but not limited to ischaemia, trauma, bacterial infection, viral infection, fungal infection, mycoplasma infection, infection with a multicellular parasite, infection with a unicellular parasite, autoimmune disease, graft host rejection of a transplanted heart, damage from cytotoxic drugs. The damage to myocardial tissue may also be the result of a genetic condition such as muscular dystrophy that leads to wasting of myocardial tissue.

Ideally, the cells used for therapy are derived from the patient's own bone marrow cells. Where this is not possible, donor cells may be used that are as closely matched as possible to limit rejection of the xenograft. In this case, immunosuppressive agents such as cyclosporine would be administered to minimise rejection of the engrafted cells.

Methods for engrafting cells to the heart are well known to the skilled artisan, and the present invention is not restricted to any one protocol. However, Applicants have found that administration using a wide bore needle or cannula is effective in delivering the cells directly into the myocardium. Alternative methods of administration include 1) catheter-based intracoronary injection, 2) catheter-based coronary transvenous injection, 3) catheter-based epicardial myocardial injection from within a coronary artery, 4) systemic infusion. Such administration could be further assisted with commercial percutaneous mapping system based on non-contact mapping methods such as Ensite 3000®, available from Endocardial Soultions, St. Paul, Minn., USA. Such a system is currently used for mapping of complicated arrhythmias and their subsequent radio-frequency ablation. It employs advance mathematical methods that provide detailed mapping of the entire endocardial surface of either the atrial or ventricular chambers by simultaneously computing electrograms and rapidly displaying high-resolution color maps of activation in the intact beating heart. There is also a catheter based non-contact multi-electrode array (MEA) to detect far field endocardial potentials from within the cardiac chamber. From these potentials, the system reconstructs instantaneous endocardial electrograms and isopotential maps on a computer generated 'virtual' endocardium. This non-contact mapping system is also capable of locating and guiding a conventional contact catheter, or a cell injection catheter to an area of interest on the isopotential cardiac map).

The non-contact catheter with its MEA is connected to a custom designed amplifier system, which is connected to a computer workstation. The workstation is designed to run specifically designed software. The system simultaneously reconstructs 3,000+ electrograms and displays them as a 3D graphical representation of the heart chamber in an isochronal or isopotential mode. With this visualization, it is possible to assess accurately areas of least contraction and electrical activity and direct cell injections around these areas.

It is contemplated the present invention will provide routine cellular transplantation for heart failure as a minimally invasive procedure much like coronary angiography and angioplasty. Patients who have exhausted all avenues of treatment will be admitted and have their bone marrow harvested. These cells will be cultured and expanded over 2 to 4 weeks using methods as previously described. Using a mapping system such as the ESI system, these autologous stem cells will then be injected into the failing heart in the cardiac catheterization laboratory.

The cells may be administered at one location or at multiple locations in the heart. Preferably the cells are administered at location(s) adjacent to the area(s) of damaged myocardium.

The engrafted CLCs may show cross-striations and align in parallel to the native cardiac myofibers thereby contributing to overall myocardial contractility and functionality. Mechanical stretching and electro-physiological signals from adjacent native myofibers may reinforce differentiation of the engrafted CLCs to mature cardiac myofibers through connexin-43 and other gap junction proteins. The distribution of CLCs in the interstitial space in close proximity to well differentiated host cardiomyocytes (FIG. 7B) is reminiscent of the reported Nkx2.5/GATA-4-expressing cardiac stem cells in the regenerating rat myocardium that are in transition to become naive cardiomyocytes. Beltrami, A. P., Barlucchi, L., Torella, D., Baker, M., Limana, F., Chimenti, S. et al. Adult cardiac stem cells are multipotent and support myocardial regeneration. *Cell*. 2003; 114:763-76.

It is likely that CLCs failed to survive in the hostile myocardial environment when transplanted early following infarction and the milieu may be less conducive for myofibrillar engraftment two weeks after infarction. In light of this, in a preferred form of the method, administration of the cardiomyocyte-like cells occurs at about 7 days to about 28 days after acute damage to the cardiomyocyte.

The results are unlikely due to host incorporation of BrdU released from necrosed CLCs since co-localization of BrdU staining with human nuclear immunoreactivity supports the specificity of BrdU labeling of human CLCs in the transplanted myocardium.

The invention will now be further described in the following non-limiting examples.

EXAMPLES

The following materials and methods were used in Examples 1 to 4 inclusive.

Recruitment of Patients

Fifteen patients scheduled for coronary artery bypass graft (CABG) surgery were recruited into the study. Informed consent was obtained from 10 male and 5 female patients (mean age=63.8 years). Proper patients' informed consent and ethics approval were obtained for the study.

Preparation of Human Sternal Bone Marrow Cells

Bone marrow from sternum was collected during CABG surgery. Approximately 0.5 to 2 ml of bone marrow were collected into a sterile tube containing 0.6% anti-coagulant citrate dextrose-A (ACD-A) solution using a 23-gauge needle. The marrow was processed immediately to remove mature blood cell lineages using antibodies against CD3, CD14, CD19, CD38, CD66b and Glycophorin-A markers (StemCell Technologies, Vancouver, Canada). The preparation was then centrifuged in a 1.077 g/ml Histopaque (Sigma, St. Louis, Mo.) density gradient and the enriched cells were collected from the interphase, resuspended in culture medium and transferred into tissue culture flasks to culture plastic adherent cells.

Culture of Cardiomyocyte-like Cells

The cells were expanded in culture medium (CM) consisting of Dulbecco's Modified Eagle's Medium-low glucose ([DMEM-LG] GIBCO; Grand Island, N.Y.) with 10% fetal bovine serum (Hyclone, Logan, Utah) or myogenic differentiation medium (MDM) consisting of 60% DMEM-LG/28% MCDB-201 (Sigma), 1.0 mg/ml bovine insulin, 0.55 mg/ml human transferrin, 0.5 µg/ml sodium selenite, 50 mg/ml bovine serum albumin, and 0.47 µg/ml linoleic acid, $10^{-4}$ M ascorbate acid 2-phosphate, $10^{-9}$ M dexamethasone, (all from Sigma), 100 units/ml penicillin G, 100 µg/ml streptomycin sulfate and 250 ng/ml amphotericin B (GIBCO) and 10% fetal bovine serum (StemCell Technologies) continuously for approximately 7 to 10 days to facilitate the formation of colonies of spindle cells. After that, fresh medium was changed every 3 days. The subconfluent cells in the seed cultures were removed from the flasks by 0.25% trypsin/EDTA (Sigma) treatment 14 to 21 days after the initial plating, expanded and labeled as passage 1 (FIG. 1).

Reverse Transcriptase-Polymerase Chain Reaction

Total RNA was extracted from cultured cardiomyocyte-like cells using Trizol reagent (GIBCO). Human cardiac RNA was purchased (Chemicon) as positive control. RNA samples were treated with RNase-free DNase (Promega, Madison, Wis.) before converted to cDNA using Superscript III first strand synthesis kit (Invitrogen, Carlsbad, Calif.). PCR primers used were listed in Table 3. All PCR was performed with Taq polymerase (Promega) for 40 cycles of 95° C. for 60 s, 60° C. for 30 s and 72° C. for 60 s, with an additional 7 minutes at 72° C. at the completion of the final cycle. Nested PCR using the condition above was used to detect GATA4, Nkx2.5 and cardiac troponin T after a primary round of PCR performed at 95° C. for 60 s, 55° C. for 30 s and 72° C. for 60 s for 35 cycles.

Antibodies and Immunostaining

Early passage cells (passage 1-5) cultured in CM or MDM were plated at $1.5 \times 10^4$ cells/cm². The cells were fixed in cold acetone/methanol (1:1), blocked in 5% bovine serum albumin ([BSA] Sigma) and incubated with primary antibodies diluted in 1% BSA for 90 minutes at room temperature. After phosphate-buffered saline (PBS) washes, Rhodamine-conjugated anti-mouse antibody (Chemicon, Temecula, Calif.) or Alexa Flour-488-conjugated anti-rabbit antibody (Molecular Probes, Eugene, Oreg.) was added to the cells for 90 minutes. Signals were visualized using a Zeiss Axiovert fluorescent microscope and images analyzed with AxioVision-4 software (Carl Zeiss, Hallbergmoos, Germany). Analysis was repeated using immunocytochemistry technique. The cells were fixed in 2% paraformaldehyde (PFA) and permeabilized with 0.1% Triton X-100. After quenching with 3% hydrogen peroxide, non-specific background was blocked by a serum-free blocking solution (DakoCytomation, Glostrup, Denmark). Primary antibodies were diluted in dilution buffer (DakoCytomation) and incubated with the cells for 60 minutes at room temperature. After PBS washes, a polymer-linked horse-radish peroxidase (HRP)-labeled secondary antibody (DakoCytomation) was added to the cells for 60 minutes. The signals were visualized using diaminobenzidine (DAB) substrate and counterstaining using hematoxylin. To detect leukocytes and endothelial cells, antibodies against CD31, CD34, CD44, CD45, CD90, CD105, CD106 and CD117 (all from Pharmingen; Becton Dickinson, Franklin Lakes, N.J.; except CD31, CD105 and CD117 were from DakoCytomation), Tie2 (Santa Cruz Biotech, Santa Cruz, Calif.), von Willebrand factor (DakoCytomation), FLK1 and FLT1 (both from Sigma) were used (Table 1). To characterize CLCs, antibodies against cardiac troponin I (USBiological, Swampscott, Mass.), desmin, sarcomeric α-actinin, sarcomeric α-tropomyosin, skeletal/cardiac-specific titin and sarcomeric and endoplasmic reticulum calcium 2 ATPase ([SERCA2 ATPase] all from Sigma), sarcomeric α-actin and connexin-43 (both from Zymed, San Francisco, Calif.), sarcomeric myosin heavy chain ([MHC] developed by D. A. Fischman and obtained from DSHB, University of Iowa, Iowa City, Iowa), cardiac-specific α/β MHC and cardiac myosin light chain-2 (both from Alexis-QBiogene, Carlsbad, Calif.), MyoD (Pharmingen), atrial natriuretic peptide (ANP) and slow muscle MHC (both from Chemicon), skeletal muscle MHC and cardiac troponin T (both from Neomarkers; Labvision, Fremont, Calif.), GATA-4 (Santa Cruz Biotech) were used (Table 2).

Bromodeoxyuridine Labeling of Cardiomyocyte-Like Cells

CLCs at about 80% confluence were incubated with 10 µM bromodeoxyuridine ([BrdU] Roche, Basel, Switzerland) in complete MDM for 24 hours to facilitate labeling and subsequent tracing of transplanted cells. The labeled cells were rinsed three times with PBS before removed by trypsin treatment and counted using a hemocytometer. Cell viability was determined to be greater than 95% and labeling efficiency was close to 65%.

Rat Myocardial Infarction Model and Cell Transplantation

Female Wistar rats weighing 200-250 grams were used to create a myocardial infarction model by ligating the left coronary artery. Mini-thoracotomy was performed after animals were anesthetized with mixture of ketamine/valium solution (10 mg/kg) under continuous intubation. Cells from a patient that showed optimal growth based on rapid proliferation rates and uniform phenotypical characteristics in culture were selected for transplantation study. A single intramyocardial injection of 100 µl containing approximately $5 \times 10^5$ early passage (passage 4-6) CLCs was administered into the peri-infarct area using a 27-gauge needle immediately (n=6), at 1 week (n=7) or 2 weeks (n=7) post-infarction via a second mini-thoracotomy. A control group (n=7) and sham-operated group (n=6) underwent the same surgical procedure but was injected 1 week post-infarction with serum-free medium or remain uninjected respectively. Animals in the cell transplanted groups were administered cyclosporine A (Novartis, Basle, Switzerland) at a dose of 10 mg/kg daily subcutaneously. Animals were sacrificed 4 weeks after transplantation. All procedures were approved by the relevant institutional animal ethics committee.

BrdU Tracking of Transplanted Cells

The animals were sacrificed 4 weeks after cell transplantation. Hearts were explanted at sacrifice and were fixed in 4% PFA and followed by immersing in a 30% sucrose solution overnight. The tissues were embedded in tissue freezing medium (Leica, Nussloch, Germany) and snap-frozen in liquid nitrogen. Serial sections of 10 µm thickness were prepared on poly-L-lysine coated slides. Antigen unmasking was performed by trypsin digestion before incubating in a denaturing solution (Zymed). Following blocking in a serum-free blocking solution (DakoCytomation), the sections were incubated with pre-diluted biotinylated mouse anti-BrdU antibody (Zymed) overnight at 4° C. followed by immunofluorescent or immunohistochemical analysis. Specificity of BrdU labeling in the transplanted myocardium was determined by staining the anti-BrdU antibody-labeled sections (described above) with anti-human nuclei antibody (Chemicon) that was conjugated with Alexa Fluor-488 using Zenon $IgG_1$ labeling kit (Molecular Probes). The BrdU signals were detected using Alexa Fluor-555-conjugated streptavidin (Molecular Probes) and nuclei were counterstained with 4',6-diamidino-2-phenyindole (DAPI). The fluorescent signals were visualized with appropriate filter sets using a Zeiss Axiovert fluorescent microscope. Morphometric study was carried out by immunohistochemical analysis of BrdU signals by incubating the anti-BrdU antibody-labeled sections (described above) with alkaline phosphatase-conjugated streptavidin solution (DakoCytomation) at room temperature. Negative controls included sections from medium-injected group or cell transplanted group with or without incubating with biotinylated anti-BrdU antibody respectively. The dark brown nuclear signals were developed using 5-bromo-4-chloro-3-indolyl phosphate/nitro blue tetrazolium/iodonitrotetrazolium violet (BCIP/NBT/INT) substrate, supplemented with levamisole solution (DakoCytomation) to block any endogenous alkaline phosphatase activity.

Large Scale Expansion of Cardiomyocyte-Like Cells

Human cardiomyocyte-like cells were cultured ($3 \times 10^3$ cells/cm$^2$) on tissue culture plates pre-coated with collagen I (10 µg/cm$^2$) or collagen V (10 µg/cm$^2$) (both from Sigma) to assess the influence of extracellular matrix on cellular proliferation. Proliferation of the cells in myogenic differentiation medium (MDM) was monitored over a period of 11 days with fresh medium change every 3 days. The cell numbers were enumerated by direct cell counting method using a hemocytometer and the overall expansion was estimated from the difference between cell numbers on first day post plating and the last day of culture. Data were gathered and computed from 3 independent experiments with triplicate plating for each matrix protein.

Electrophysiologically Guided and Targeted Percutaneous Cell Delivery into Peri-Infarcted Area of Infarcted Swine Heart A 35 to 70 kg pig was sedated with intramuscular (IM) injection of ketamine (7 mg/kg) and acetyl-promazine (0.2 mg/kg). The pig was intubated through the mouth and remained anesthetized with 1-3% isoflurane in 100% oxygen. A baseline cardiac ultrasound was then performed. Bone marrow aspiration was performed through the iliac crest under sterile conditions to acquire up to 20-50 ml of bone marrow. The bone marrow was processed and cultured as described for human bone marrow cells. Swine CLCs were confirmed using expression profiles described as above. Left surgical thoracotomy was performed and the left circumflex artery ligated at its mid-segment. Left circumflex coronary occlusion was confirmed under fluoroscopy with contrast injection into the left coronary system. Thoracotomy was surgically closed. The animal's blood pressure, oxygen saturation and electrocardiogram were monitored continuously post-extubation until it recovered from anesthesia. Post procedural pain was managed with IM administered buprenorphine (0.03-0.3 mg/kg). At 2-4 weeks after creation of myocardial infarct. Animals were prepared for cell injection and anaesthetized as previously described. Cardiac ultrasound was performed to confirm presence of myocardial infarction and to confirm location of the infarction. A 9-French (F) sized sheath was inserted in the right femoral artery while a 6-F sheath was inserted in the left carotid artery.(in man, this sheath will be placed in the contralateral groin).Under fluoroscopic guidance, the ESI non-contact MEA catheter (Endocardial Solutions Inc.) was placed in the left ventricle via the femoral sheath. A second roving catheter was placed from the left carotid sheath into the left ventricle. This second catheter aids the construction of a 3D computer model of the endocardium with precise location of the area of damaged myocardial tissue. The second catheter would be removed from the sheath once the mapping was completed. Using this 3D map and fluoroscopic guidance, a bipolar tipped injection catheter was then be inserted via the left carotid sheath into the left ventricle. Up to 10-20 injections, each containing approximately $5 \times 10^5$ DiI fluorescent dye (Molecular Probes) labelled cells in 0.1 ml was injected using the injection catheter guided by ESI around the peri-infarct region. Animals were monitored post injection and managed as described above. Six to 8 weeks after the cellular transplantation a second echocardiogram was performed on the animals to document the size of infarct, viability of myocardium and ejection fraction. A repeat electrophysiology study using the ESI was performed to gauge improvements in damaged myocardial areas. The animals were sacrificed and hearts excised. Wide-field and confocal fluorescent microscopy was performed on tissue sections to locate the injected cells.

Example 1

Proliferation of Cardiomyocyte-Like Cells in Culture

Figure 2:
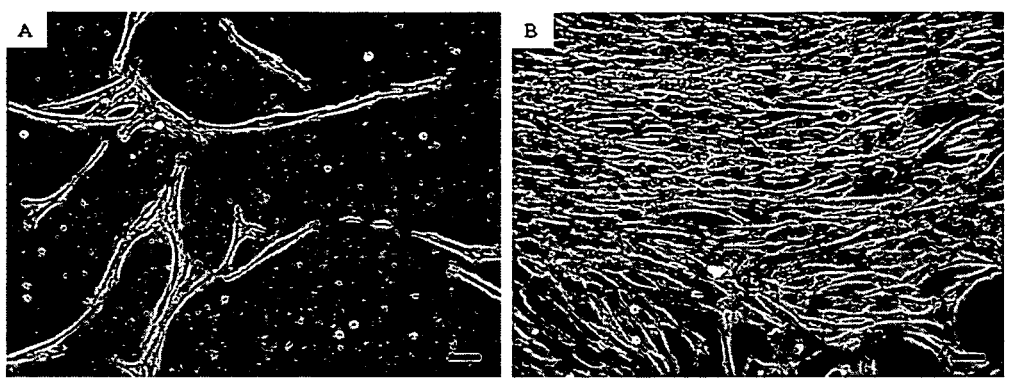
FIGS. 2(A) and (B). are light micrographs showing the spindle morphology of adult human bone marrow-derived cells. (A) isolated spindle cells 3 to 4 days after seeding in culture. (B) subconfluent colony of spindle cells 10 to 14 days after isolation. Scale bar, 20 μm.
Figure 3:
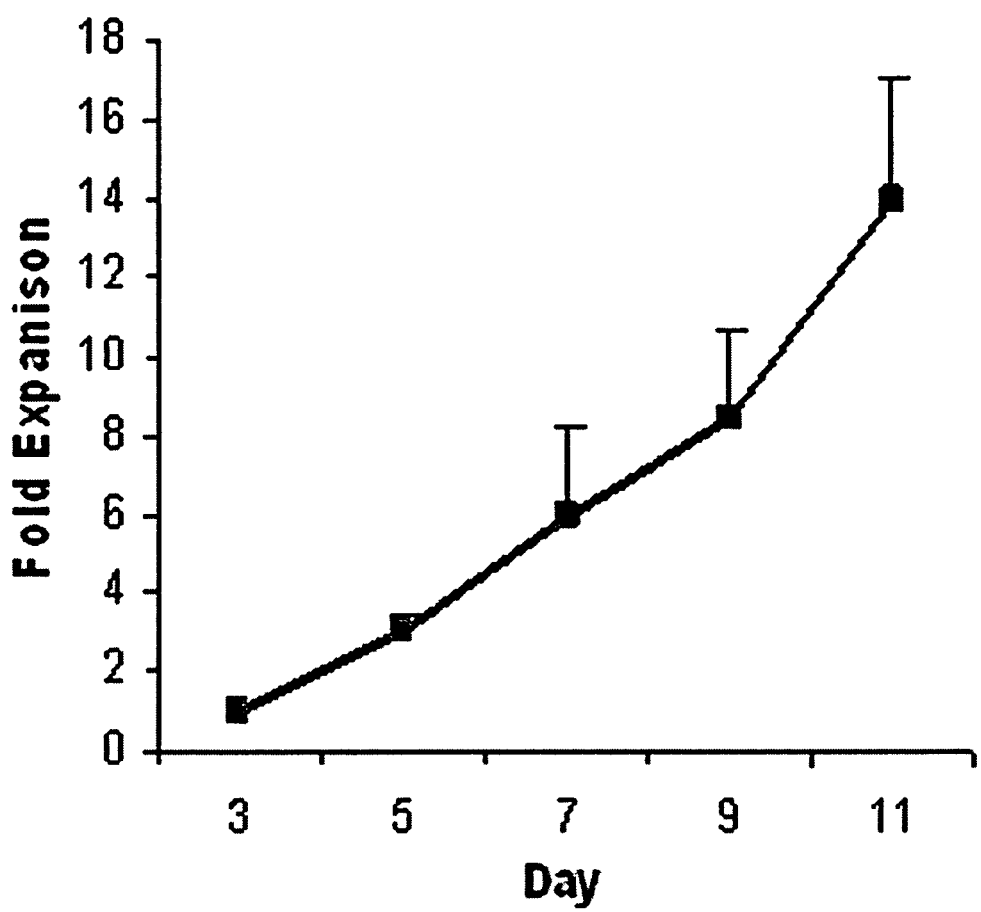
FIG. 3. is a graph showing growth kinetics of cardiomyocyte-like cells in culture. Early passage cells were plated at 3000 cells/cm$^2$. Cell growth was monitored by manual cell count using a hemocytometer. Data presented as mean±SD (n=20) per time point.

Cells from a total of 12 patients were successfully expanded and used for subsequent analyses (FIG. 1). Marrow from 3 other patients failed to form viable cultures due to sparse starting cell numbers. Single cells of spindle morphology were observed 3 to 4 days after the initial seeding in culture. They rapidly expanded into colonies of confluent spindle cells with approximately 1 to 2 thousand cells in the next 7 days (FIG. 2A and B). Most of the loosely attached round hematopoietic cells were removed following medium change. Cultured cells were mainly of spindle morphology with an average doubling time of 48 to 72 hours (FIG. 3) but 5 to 10% of the colonies consisted of cells of polygonal morphology. After prolonged passages (>10 passages) in culture, the cells progressively lost their spindle morphology and the cultures were increasingly dominated by cells with polygonal morphology with an average doubling time of more than 96 hours.

Example 2

Cardiomyocyte-Like Cells Are Negative for Endothelial Phenotypes

Figure 4:
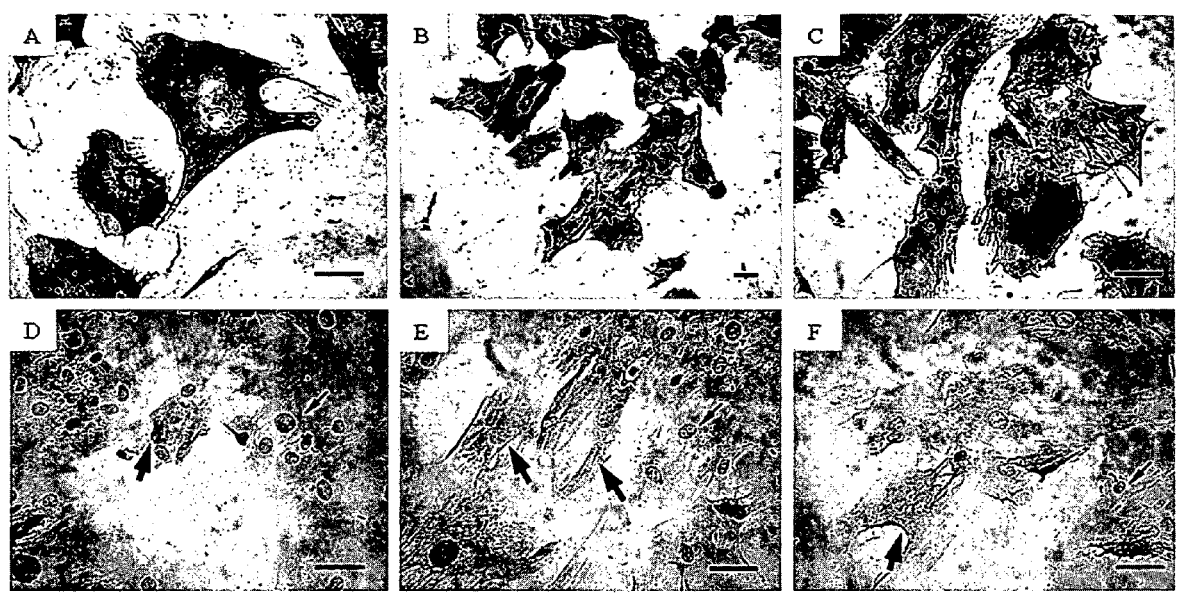
FIG. 4(A) to (F) are immunohistochemistry micrographs showing human adult cardiomyocyte-like cells express mesenchymal and hematopoietic markers. (A) CD44. (B) CD90. (C) CD105. (D) CD106. (E) CD34. (F) FLK1. (thick and thin arrows indicate positively and negatively stained cells respectively in D, E and F). Scale bar, 20 μm.
Figure 5:
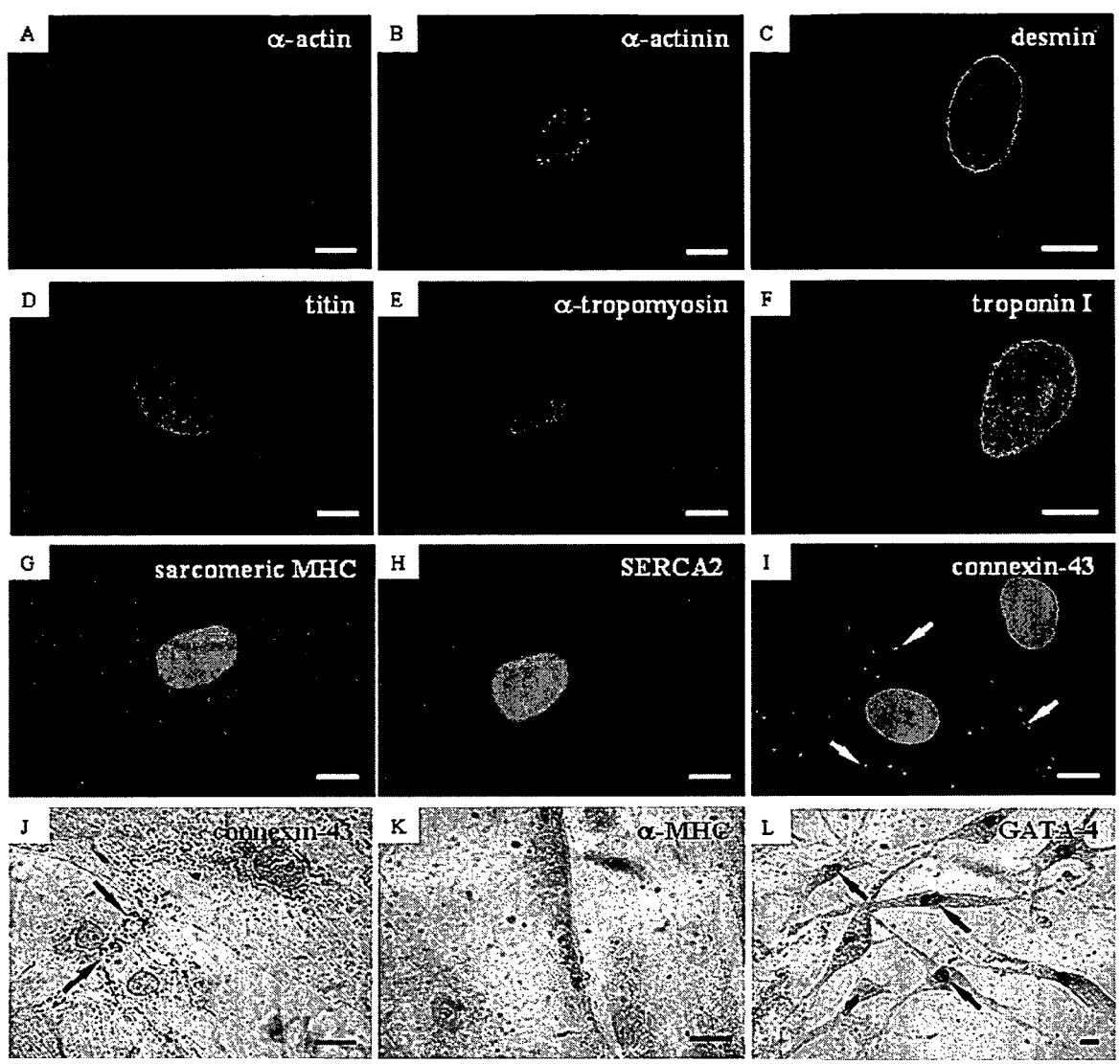
FIG. 5(A) to (I) are immuofluorescence micrographs.
FIG. 5(J) to (L) are immunohistochemistry micrographs of human adult cardiomyocyte-like cells showing the expression of multiple contractile and sarcomeric proteins. (A) sarcomeric α-actin. (B) sarcomeric α-actinin. (C) desmin. (D) skeletal/cardiac-specific titin. (E) sarcomeric α-tropomyosin. (F) cardiac troponin I. (G) sarcomeric myosin heavy chain. (H) SERCA2 ATPase. (I&J) connexin-43 (arrows indicate gap junction). (K) cardiac-specific α/β myosin heavy chain. (L) GATA-4 (arrows indicate positively stained nuclei). Scale bar, 20 μm.

The MDM cultured cells showed positive staining for markers such as CD44, CD90, CD105 and CD106 (FIG. 4A to D) but were negative for CD45 and CD117 (Table 1). The cells showed about 30% positive staining for CD34 and FLK1 markers (FIGS. 4E and F) but were negative for Tie2, von Willebrand factor (vWF), CD31 and FLT1 endothelial markers (Table 1). These may represent residual hematopoietic cells from the initial cultures or they may be a subpopulation of bone marrow cells that expresses both mesenchymal and hematopoietic markers, since over 99% of the cells were stained positive for CD44, CD90 and CD105 mesenchymal markers.

Example 3

Cardiomyocyte-Like Cells Exhibit Cardiac but not Skeletal Muscle Characteristics Approximately 1% of the cells in the colonies were stained positive for cardiac troponin I 2 weeks after first seeding in MDM. After 4 to 5 passages, more than 90% of the cells were consistently stained positive for sarcomeric α-actin, sarcomeric α-actinin, desmin, skeletal/cardiac-specific titin, sarcomeric α-tropomyosin, cardiac troponin I, sarcomeric MHC, SERCA2 ATPase and connexin-43 (FIG. 5A to J). Expression of troponin I and SERCA2 ATPase was detected early (passage 1-2) followed by titin and desmin (passage 2-3) and then tropomyosin and actinin (passage 3-5) indicating differentiation towards CLCs. Approximately 60% of the CLCs also stained positive for cardiac-specific α/β MHC and cardiac transcription factor GATA-4 (FIGS. 5, K and L) suggesting a developing cardiomyocyte phenotype. There was weak immunoreactivity with slightly above background staining against ANP and cardiac troponin T and no staining for myosin light chain-2. The CLCs were negative for MyoD, skeletal and slow muscle MHC (Table 2), precluding skeletal muscle nature of the cells. Similar myocardial profile was consistently detected in MDM cultured CLCs from 9 patients tested. These characteristics were maintained for more than 10 passages and also in cultures re-established after cryopreservation. Myofibrillar structures in cross-striated Z-band arrangement (FIG. 6) were detected but no spontaneous beating were observed in the cultured cells. Similarly isolated early passage cells from 3 patients that were maintained in CM were consistently negative for α-actin, α-actinin, desmin, titin, tropomyosin and troponin I (Table 2).

Example 4

Figure 7:
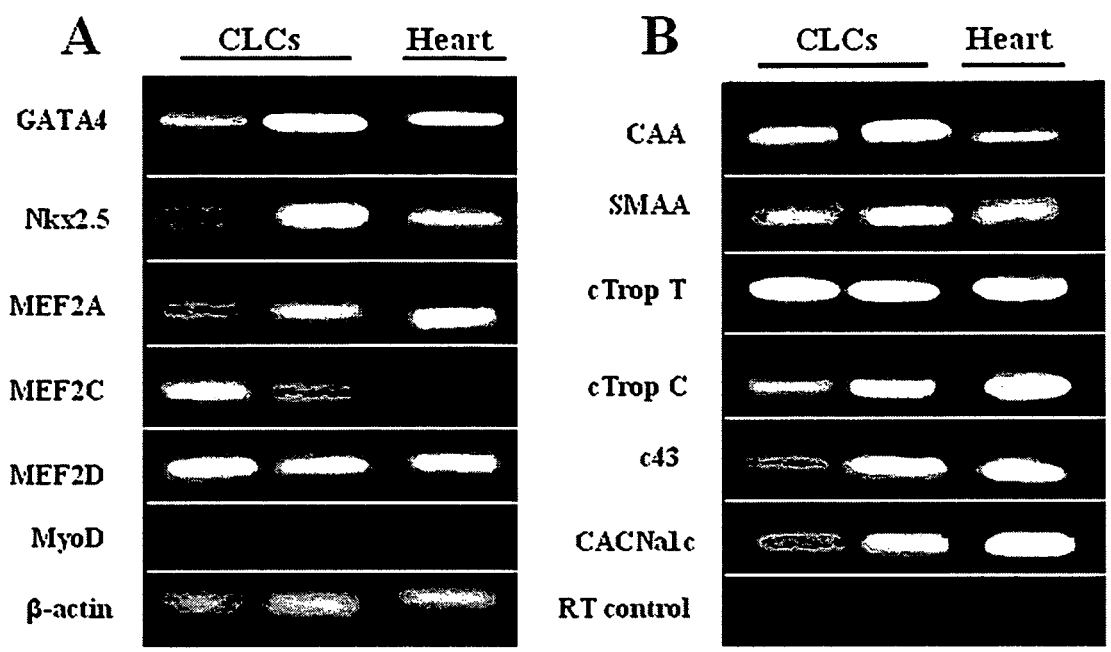
FIGS. 7(A) and (B) are DNA gel electropheresis micrographs showing human cardiomyocyte-like cells express cardiac transcription factors, cardiomyofibrillar and electrophysiological genes closely associated with cardiomyocytes. Results from 2 representative human bone marrow samples in differentiated cultures. c43: connexin43, MEF: myocyte enhancing factor, CAA: cardiac α-actin, SMAA: skeletal muscle α-actin, cTrop T: cardiac troponin T, cTrop C: cardiac troponin C, CACNA1c, L-type calcium α1c channel. CLC: cardiomyocyte-like cells, Heart: human heart cDNA. RT control: reaction without reverse transcriptase.
Figure 8:
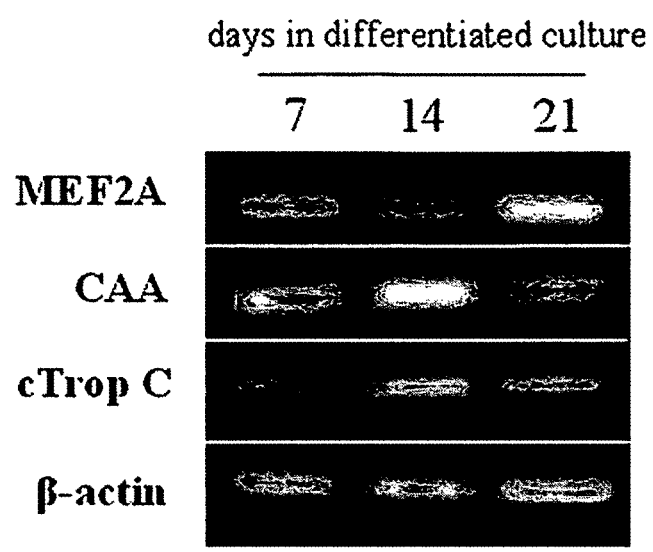
FIG. 8. is DNA gel electropheresis micrograph demonstrating cardiomyocyte-like cells showing stable temporal expression of the cardiac markers in culture. CAA: cardiac α-actin, cTrop C: cardiac troponin C, MEF: myocyte enhancing factor.

Cardiomyocyte-Like Cells Show Consistent Multiple Cardiac-Specific Gene Expression The spindle cells that were cultured in the myogenic differentiation medium (MDM) become cardiomyocyte-like cells with multiple cardiac-specific gene expression. The differentiated cell expressed cardiac lineage transcription factors, such as GATA4, Nkx2.5, MEF2A, MEF2C and MEF2D, but not MyoD that is restricted to skeletal muscle lineage (FIG. 7, A). These cells also expressed structural genes in the sarcomeric myofilaments, such as cardiac α-actin, skeletal muscle α-actin, cardiac troponin T and cardiac troponin C (FIG. 7, B). These cardiomyocyte-like cells also expressed genes that are involved in the excitation-contraction coupling of cardiac muscles, such as connexin43 and L-type $\alpha_{1c}$ calcium channel (FIG. 7, B). The cardiac gene expression was stable in the differentiated culture with consistent expression profile detected in cells that were cultured for 7, 14 and 21 days (FIG. 8). This cardiac gene expression profile was also maintained after successive sub-culturing of the cells for more than 10 passages.

Example 5

Myofibrillar Engraftment of Transplanted Cardiomyocyte-Like Cells

Figure 9:
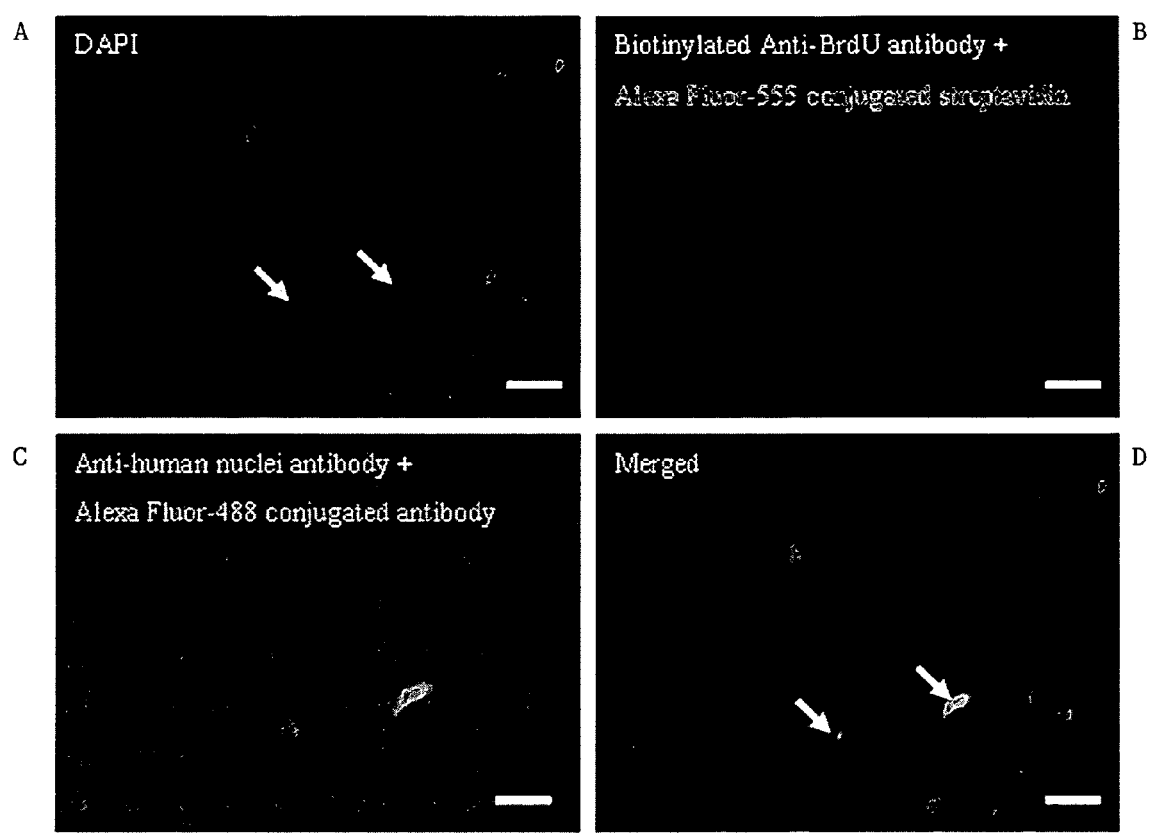
FIG. 9(A) to (D) are immunofluorescence micrographs showing the specific localization of BrdU in human cardiomyocyte-like cells in infarcted rat myocardium. (A) nuclear staining by DAPI showing rat and human (arrows) nuclei. (B) engraftment of BrdU-labeled cells in rat myocardium. (C) engraftment of human cells in rat myocardium. (D) merged images of A, B and C demonstrating co-localization of BrdU-labeled nuclei with human nuclei (arrows). Scale bar, 20 μm.
Figure 10:
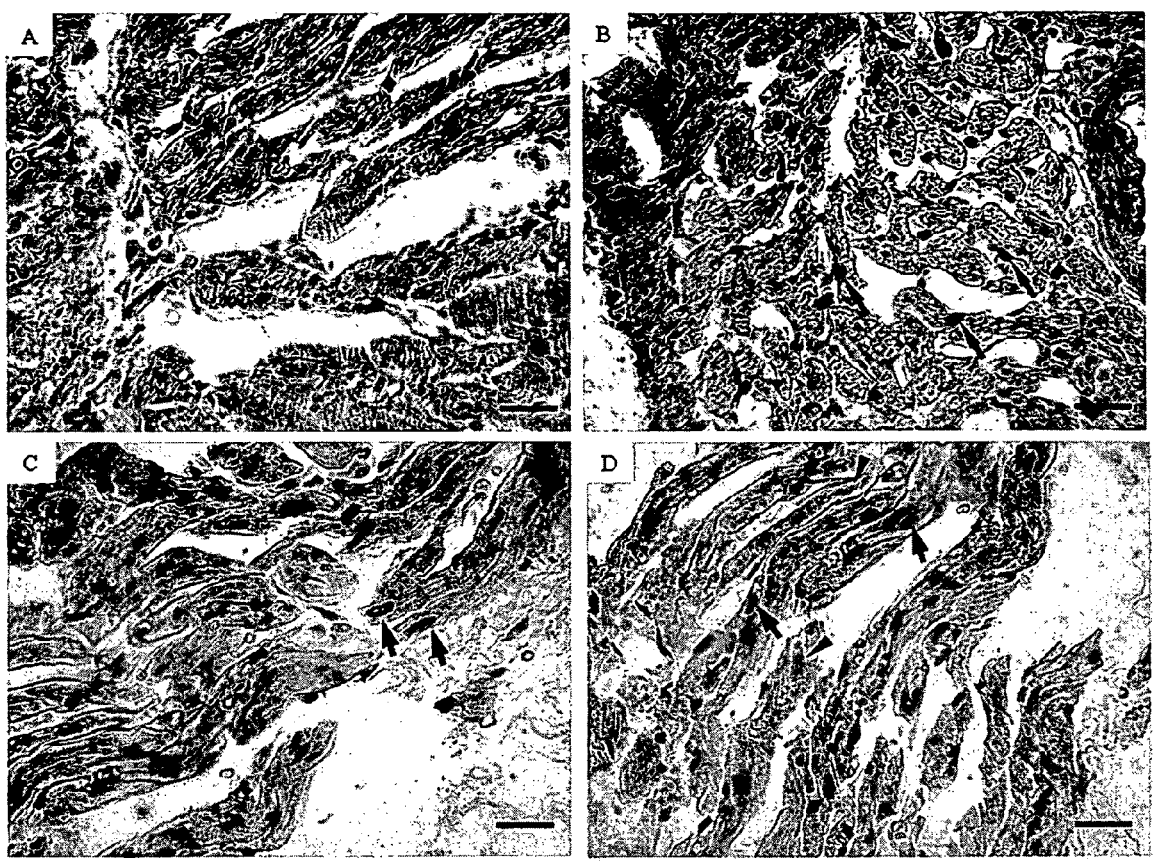
FIG. 10(A) to (D) are immunohistochemistry micrographs showing the integration of cardiomyocyte-like cells into cardiac myofibers in the peri-infarct areas. (A) absence of BrdU-labeled cells in negative control section from medium-injected heart. (B) localization of CLCs (arrows) in close proximity to host cardiac myofibers. (C) engraftment of cross-striated CLCs with centrally located BrdU-labeled nuclei (arrows) in cardiac myofibers. (D) BrdU-labeled CLCs (arrows) aligned in parallel to the host cardiac myofibers (arrowheads). Scale bar, 20 μm.

BrdU immunoreactivity was found to co-localize with anti-human nuclei immunofluorescence signals in the infarcted myocardium thereby supporting the specificity of BrdU in tracking the transplanted cells (FIG. 9). BrdU-labeled CLCs were detectable in 2/6, 4/7 and 5/7 animals in acute, 1-week and 2-week post-infarct transplanted groups respectively. Most of the BrdU-labeled CLCs remained in the surrounding regions of the injected side of the peri-infarct with a significant number of cells located in the interstitial space in close proximity to host cardiac myofibers in all 3 transplanted groups (FIG. 10, B). The CLCs transplanted 1 week post-infarction engrafted distinctly as cardiac myofibers. The engrafted myofibers displayed characteristic cross-striations (FIG. 10, C) with centrally located nuclei that aligned parallel (FIG. 10, D) to the native cardiac myofibers that are suggestive of a specific and orderly integration into the myofibrillar structures.

Example 6

Large Scale Cardiomyocyte-Like Cell Expansion for Cell Therapy

Figure 11:
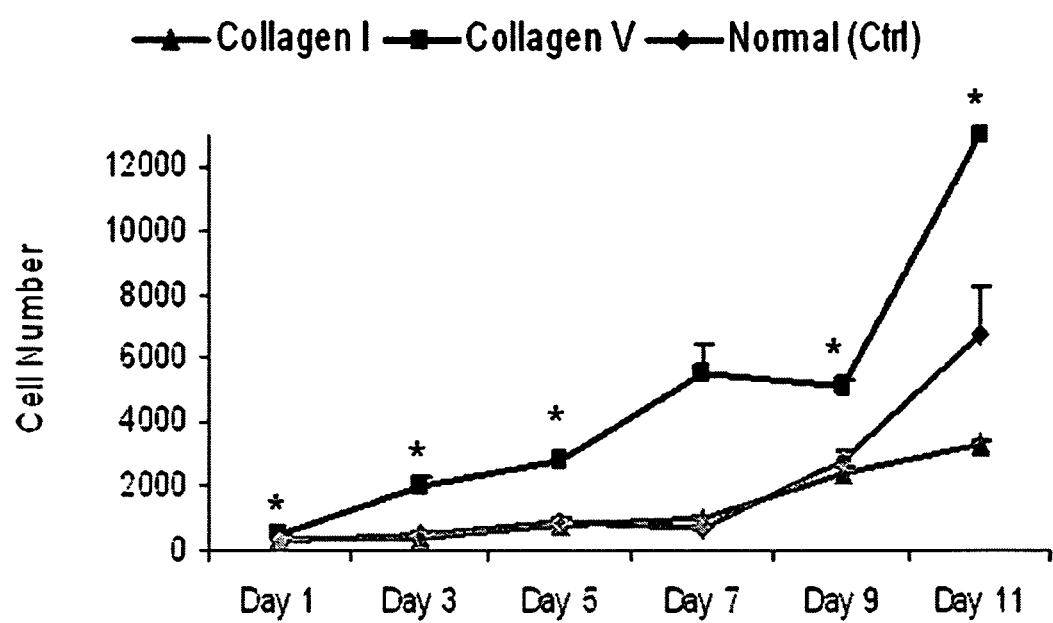
FIG. 11. is a graph showing large scale expansion of cardiomyocyte-like cells in culture using extracellular matrix protein. Collagen V matrix promoted attachment and proliferation of human cardiomyocyte-like cells in culture. *p<0.05 versus control tissue culture flask surface.

Human cardiomyocyte-like cells interacted preferentially with collagen V matrix resulting in more than 20 folds expansion in cell numbers within 2 weeks of culture. Collagen V enhanced cell attachment on the first day of cell seeding and resulted in significant cell expansion in culture. Collagen I matrix failed to show significant effect in promoting cell attachment and proliferation (FIG. 11). Therefore, collagen V matrix may be potentially useful for scaling up production of these cells for large scale cell transplantation to repair damaged myocardium.

Example 7

Figure 12:
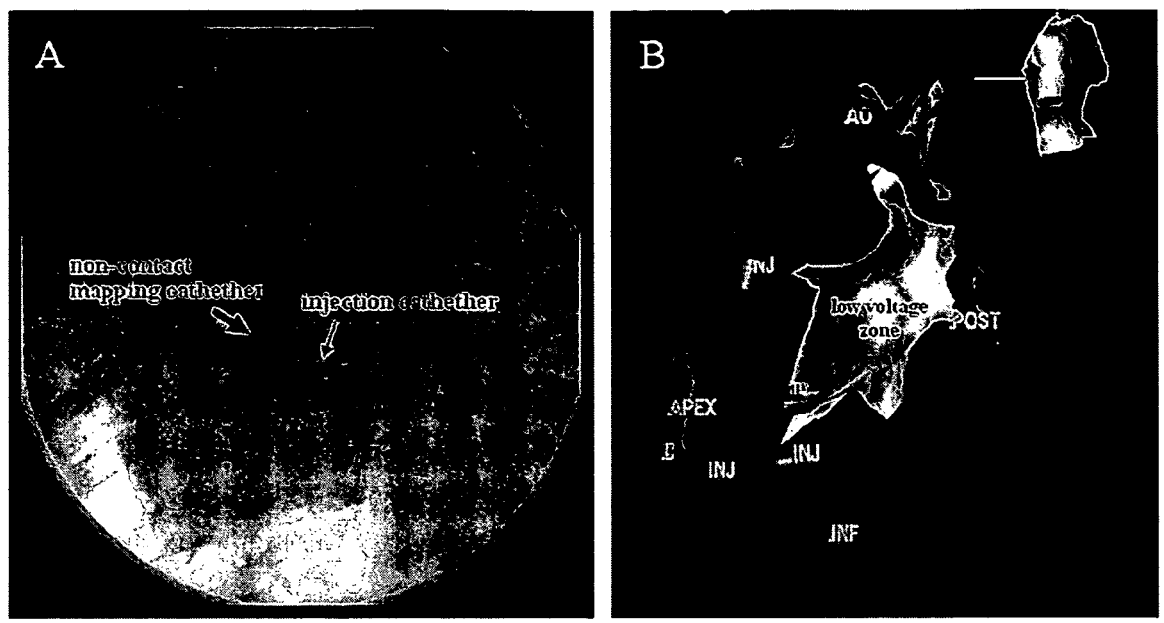
FIGS. 12(A). and (B). are micrographs showing injection of autologous cardiomyocyte-like cells into pig myocardium. (A) fluoroscopic image showing use of non-contact electrophysiological device (thick arrow) within the left ventriculogram to direct and guide percutaneous intramyocardial injections (thin arrow) of autologous cardiomyocyte-like cells into the myocardium. (B) electrical map with low voltage zone highlighting areas of infarcted myocardium and pinpointing accurately in a 3-dimensional left ventricular map the exact locations of percutaneous injections (marked INJ) of autologous cardiomyocyte-like cells. AO: aorta, INF: inferior, POST: posterior.
Figure 13:
FIG. 13. are micrographs showing percutaneously-delivered autologous pig cardiomyocyte-like cells engrafted in the infarcted myocardium following electrophysiologically guided injection into borders of the electrically inactive infarcted zone. Arrowheads indicate regions of transplanted cells. Arrows indicate Dil labeled pig cells survived in the myocardium. Scale bar: 5 μm.

Cardiomyocyte-Like Cells Engrafted in Infarcted and Peri-Infarcted Myocardial Tissue after Electrophysiological Guided Injections of Autologous CLCs in Swine Infarct Model Pig bone marrow cells were derived and differentiated similarly as described for human cardiomyocyte-like cells for autologous transplantation. The pig cells were DiI fluorescent dye (Molecular Probes) labelled (2 µM) and resuspended in a final concentration of $5 \times 10^6$ cells/ml for injection through a bipolar electrical tipped injection catheter (FIG. 12, A). The pig heart was mapped electrically using the ESI non-contact mapping system (Endocardial Solutions Inc.) to track the cardiac electrical activity as dynamic waveforms and 3D isopotential maps that display a range of electrical potentials across the entire surface of endocardium. Infarcted areas were clearly seen as distinct low voltage areas (FIG. 12, B). The labelled cells were injected via a percutaneous injection catheter ($5 \times 10^5$ cells/0.1 ml/injection in a total of 5-20 injections) into the infarcted borders of the electrically mapped swine's heart guided by the 3D contoured isopotential maps and x-ray fluoroscopy for targeted delivery. The DiI labelled pig cells were found to survive and localize in the proximity of the infarcted borders 4-8 weeks post-injection (FIG. 13) demonstrating the feasibility of selective targeting of these cells for therapeutic transplantation.

Example 8

Prophetic Example: Treatment of Human Patients with Cardiomyocyte-Like Cells Preparation of the patient will be similar to that for PCI. Patients will be admitted and have bone marrow harvested from the iliac crest or sternum. Stem cells will then be cultured as outlined herein and injected back into the patient via a catheter-based, minimally invasive method 3-4 weeks after bone marrow is first harvested. CLCs will be injected and targeted directly into the myocardium at areas of damage as defined by electrophysiological mapping and guided by fluoroscopy. Access for a minimally invasive method will be via the Femoral or Radial arteries. An advantage of the minimally invasive method is that it can be repeated several times if the CLC injections prove beneficial to the patient.

The cells will be injected intramyocardially via the left ventricle. Other potential methods will be intracoronary injections, transvenous injections via the coronary veins and trans-epicardial injections through the coronary arteries will also be suitable.

Success of the procedure will be quantified by a decrease in symptoms, or increase in the left ventricular function as measure by Echocardiography, Angiography, MUGA scan, or MRI scan.

Finally, it is to be understood that various other modifications and/or alterations may be made without departing from the spirit of the present invention as outlined herein.

TABLE 1

Human mesenchymal stem cells co-express mesenchymal and hematopoietic markers

| Antibody | Dilution | Results |
|---|---|---|
| CD34, clone 581 | 1:10 | + |
| CD44, clone G44-26 | 1:1000 | +++ |
| CD90, clone 5E10 | 1:1000 | +++ |
| CD105, clone SN6h | 1:1000 | +++ |
| CD106, clone 51-10C9 | 1:1000 | ++ |
| FLK1, clone KDR2 | 1:50 | + |
| CD31, clone JC70A | 1:40 | − |
| CD45, clone HI30 | 1:100 | − |
| CD117, clone 104D2 | 1:400 | − |
| Tie2, polyclonal | 1:100 | − |
| von Willebrand factor, polyclonal | 1:1000 | − |
| FLT1, clone FLT-19 | 1:100 | − |

Intensity of staining: "+": positive, "++": moderately positive, "+++": strongly positive, "−": negative.

TABLE 2

Human cardiomyocyte-like cells express cardiac but not skeletal muscle markers

| Antibody | Detection Immunofluorescent | Methods Immunocytochemistry | MDM Differentiated Cells (n = 10) | CM Maintained Cells (n = 3) |
|---|---|---|---|---|
| sarcomeric α-actin, clone ZMSA5 | 1:5 | 1:25 | +++ | − |
| sarcomeric α-actinin, clone EA-35 | 1:100 | 1:400 | +++ | − |
| desmin, clone DE-U-10 | 1:50 | 1:400 | ++ | − |
| skeletal/cardiac titin, clone T11 | 1:10 | 1:50 | +++ | − |
| sarcomeric α-tropomyosin, clone CH1 | 1:10 | 1:50 | +++ | − |
| cardiac troponin I, clone 2Q1100 | 1:100 | 1:1000 | +++ | − |
| SERCA2 ATPase, clone IID8 | 1:50 | 1:2500 | +++ | ND |
| connexin43, polyclonal | 1:100 | 1:100 | ++ | ND |
| sarcomeric MHC, clone MF20 | 1:10 | 1:50 | +++ | ND |
| cardiac α/β MHC, clone F26.2D11 | ND | 1:10 | + | ND |
| GATA4, polyclonal | ND | 1:200 | ++ | ND |
| cardiac troponin-T, clone 13-11 | ND | 1:50 | +/− | ND |
| atrial natriuretic peptide, clone 23/1 | ND | 1:100 | +/− | ND |
| myosin light chain-2, clone F109.3E1 | ND | 1:10 | − | ND |
| MyoD, clone 5.8A | ND | 1:100 | − | ND |
| skeletal muscle MHC, clone MY-32 | ND | 1:100 | − | ND |
| slow muscle MHC, clone NOQ7.5.4D | ND | 1:100 | − | ND |

Intensity of staining was based on immunocytochemistry: "+/−": weakly positive, "+": positive, "++": moderately positive, "+++": strongly positive, "−": negative, ND: not determined. MDM: myogenic differentiation medium, CM: normal growth medium

TABLE 3

RT-PCR primer sequences and product sizes

| Gene | Accession no | Primer sequence | Product size |
|---|---|---|---|
| CAA | NM_005159 | 5'-CTTCTAAGATGCCTTCTCTCTCC A-3'<br>5'-TATTAGAAGCACAAACAAAT TGCA-3' | 143 bp |
| CACNA1c | NM_000719 | 5'-TGATGTGGTC TTGCACATGT G-3'<br>5'-GTAGTCACTG GTGTGCACGG-3' | 200 bp |
| c43 | NM_000165 | 5'-TGTGGACATG CACTTGAAGC-3'<br>5'-GGATCAGCAA GAAGGCCAC-3' | 152 bp |
| GATA4 | NM_002052 | 5'-TCAAATTGGGATTTTCCGGA-3'<br>5'-GCACGTAGACTGGCGAGGA-3' | 347 bp |
| GATA4 nested | — | 5'-AGCCCTTTGCTCAATGCTG-3'<br>5'-GCTCTGATAC ATGGTCCCTG C-3' | 204 bp |
| MEF2A | NM_005587 | 5'-TCCAATTGTGCTTGGCCGA-3'<br>5'-ACATACACACACACTCACACCCA-3' | 247 bp |
| MEF2C | NM_002397 | 5'-GACTTTCTGAAGGATGGGCAA-3'<br>5'-CAAGTGCTAAGCTTATCTCAGCA-3' | 230 bp |
| MEF2D | NM_005920 | 5'-TGAAGATCCCCCGGACCA-3'<br>5'-CTCGTCGGTGATTCGCTGGA-3' | 253 bp |
| MyoD | X56677 | 5'-CAGAAAGT TCCGGCCACT C-3'<br>5'-TCCGTTGT GGCAAAGGAG-3' | 152 bp |
| Nkx2.5/Csx | NM_004387 | 5'-AGCCCTGGCTACAGCTGCA-3'<br>5'-TGGGAGCCCCTTCTCCCCA-3' | 262 bp |
| Nkx2.5 nested | — | 5'-GATTCCGCAGAGCAACTCG-3'<br>5'-GGAGCTGTTGAGGTGGGATCG-3' | 105 bp |
| SMAA | AF182035 | 5'-AGACACACTCCACCT CCAGCA-3'<br>5'-CTTCCACAGG GCTTTGTTTCGA-3' | 205 bp |
| cTrop C | AF020769 | 5'-TACA AGGCTGCGGT AGAGCA-3'<br>5'-ACTCCACACC CTTCATGAAC TCCA-3' | 469 bp |
| cTrop T | AY277394 | 5'-AGGAGTCCAAACCA AAGCCCA-3'<br>5'-CTA TTTCCAGCGCCCGGTGA-3' | 677 bp |
| cTrop T nested | — | 5'-AAGCGCATG GAGAAGGACC-3'<br>5'-GTCGAGCCCTCTCTTCAGC-3' | 199 bp |
| β-actin | NM_001101 | 5'-CTTTCGTGTAAATTATGTAATGCA-3'<br>5'-TACATCTCAAGTTGGGGA-3' | 129 bp |

CAA: cardiac α-actin, c43: connexin43, CACNA1c: L-type α₁c calcium channel, SMAA: skeletal muscle α-actin, cTrop T: cardiac troponin C, cTrop T: cardiac troponin T.

We claim:

1. An ex vivo method for culturing a cell with sarcomeric myofilaments, the method consisting of:
   a) culturing a mesenchymal stem cell from a human bone marrow cell population in a culture vessel with a medium comprising dexamethasone and, optionally, a supplement selected from the group consisting of insulin, an iron source, a trace element, a fatty acid, an antioxidant, transferrin, linoleic acid, selenium, and ascorbate either alone or in any combination;
   wherein said culturing is carried out
      (i) in the absence of myocytes,
      (ii) in a medium which is not conditioned by co-culture with other cells; and
      (iii) in a medium which is lacking 5-azacytidine;
   the presence of dexamethasone leading to differentiation of the mesenchymal stem cell, such that colonies of spindle cells are formed; and
   b) isolating and expanding said colonies of spindle cells thereby isolating cells with sarcomeric myofilaments and that express one or more markers selected from the group consisting of sarcomeric α-actin, sarcomeric α-actinin, desmin, skeletal/cardiac-specific titin, sarcomeric α-tropomyosin, cardiac troponin I, sarcomeric MHC, SERCA2 ATPase, connexin-43, GATA-binding protein 4, Nkx2.5, myocyte-enhancing factor 2A, myocyte-enhancing factor 2C, myocyte-enhancing factor 2D, cardiac α-actin, skeletal muscle α-actin, cardiac troponin T, cardiac troponin C, and L-type calcium α light chain.

2. The method according to claim 1 wherein the cell population is obtained from a hollow bone.

3. The method according to claim 2 wherein the cell population is obtained from the iliac crest or the sternum.

4. The method according to claim 1 wherein the cell population is substantially free of mature cells of a blood lineage.

5. The method according to claim 1, wherein the medium is a defined cell culture medium.

6. The method according to claim 5 wherein the defined cell culture medium is free of a biological agent secreted from a rat myocyte.

7. The method according to claim 5 wherein the medium is comprises Dulbecco's Modified Eagle's Medium-low glucose (DMEM-LG) or Molecular Cellular Developmental Biology-201 (MCDB-201), or a mixture of about 60% DMEM-LG and 28% MCDB-201 augmented with fetal bovine serum.

8. The method according to claim 1 wherein the colonies of spindle cells are maintained in culture for a period of about 7 days to about 10 days.

9. The method according to claim 1 wherein the colonies of spindle cells are maintained in culture for a period of about 14 days to about 21 days.

10. The method according to claim 1, wherein said culturing comprises culturing the mesenchymal stem cell on a collagen matrix.

11. The method according to claim 10 wherein the collagen matrix is a collagen V matrix.

12. The method according to claim 1, wherein the medium contains at least one supplement selected from the group consisting of insulin, an iron source, a trace element, a fatty acid, an antioxidant, transferrin, linoleic acid, selenium, and ascorbate.

* * * * *

UNITED STATES PATENT AND TRADEMARK OFFICE
CERTIFICATE OF CORRECTION

| | | |
|---|---|---|
| PATENT NO. | : 8,513,011 B2 | Page 1 of 1 |
| APPLICATION NO. | : 11/210950 | |
| DATED | : August 20, 2013 | |
| INVENTOR(S) | : Winston Se Ngie Shim et al. | |

It is certified that error appears in the above-identified patent and that said Letters Patent is hereby corrected as shown below:

On the Title Page
Item (73), please delete the assignee "Biotech Research Ventures Pte Limited" and insert therefor
-- National Heart Centre of Singapore Pte Ltd --.

Signed and Sealed this
Fourth Day of March, 2014

Michelle K. Lee
*Deputy Director of the United States Patent and Trademark Office*